United States Patent
Kreitenberg

(10) Patent No.: US 11,045,567 B2
(45) Date of Patent: *Jun. 29, 2021

(54) OPERATOR SHIELDED MANUALLY TRANSPORTABLE ULTRAVIOLET DISINFECTION CART

(71) Applicant: DIMER, LLC, Los Angeles, CA (US)

(72) Inventor: Arthur Kreitenberg, Los Angeles, CA (US)

(73) Assignee: DIMER, LLC, Los Angeles, CA (US)

( * ) Notice: Subject to any disclaimer, the term of this patent is extended or adjusted under 35 U.S.C. 154(b) by 214 days.

This patent is subject to a terminal disclaimer.

(21) Appl. No.: 15/902,269

(22) Filed: Feb. 22, 2018

(65) Prior Publication Data

US 2018/0256764 A1 Sep. 13, 2018

Related U.S. Application Data

(60) Provisional application No. 62/469,930, filed on Mar. 10, 2017.

(51) Int. Cl.
*A61L 2/10* (2006.01)
*A61L 2/26* (2006.01)
(Continued)

(52) U.S. Cl.
CPC ...... *A61L 2/10* (2013.01); *A61L 2/24* (2013.01); *A61L 2/26* (2013.01); *A61L 9/20* (2013.01);
(Continued)

(58) Field of Classification Search
CPC ..... A61L 2/10; A61L 9/20; A61L 2/24; A61L 2/26; A61L 2209/212; A61L 2202/14;
(Continued)

(56) References Cited

U.S. PATENT DOCUMENTS 8,907,304 B2 * 12/2014 Kreitenberg ....... B64D 11/0007
250/492.1
8,999,238 B2 * 4/2015 Kreitenberg ....... B64D 11/0007
422/24
(Continued)

FOREIGN PATENT DOCUMENTS

| CN | 2705163 Y | 6/2005 |
|---|---|---|
| CN | 105944127 A | 9/2016 |
| WO | 2016/164364 A1 | 10/2016 |

OTHER PUBLICATIONS

International Search Report and Written Opinion to corresponding International Application No. PCT/US18/19143 dated May 17, 2018 (10 pages).
(Continued)

*Primary Examiner* — Sean E Conley
*Assistant Examiner* — Brendan A Hensel
(74) *Attorney, Agent, or Firm* — Greenberg Traurig, LLP

(57) ABSTRACT

A mobile body is configured to travel an area optionally over a surface inside an aircraft cabin. Components comprise at least one of a UVC protective shield, the shield selectively providing a multisided enclosure that selectively envelopes and/or separates the operator from the UVC in the surrounding environment. A source of UV radiation is mounted to the mobile body and configured to direct UV radiation to the surface at a predetermined dosage. At least two articulated arms are mounted to the mobile body, and UV lamps mounted respectively on the arms. The mobile body is a trolley or cart for negotiating an area optionally an aircraft aisle.

27 Claims, 16 Drawing Sheets

(51) Int. Cl.
*A61L 9/20* (2006.01)
*A61L 2/24* (2006.01)

(52) U.S. Cl.
CPC ........ *A61L 2202/11* (2013.01); *A61L 2202/12* (2013.01); *A61L 2202/14* (2013.01); *A61L 2202/16* (2013.01); *A61L 2202/25* (2013.01); *A61L 2209/212* (2013.01)

(58) Field of Classification Search
CPC ............. A61L 2202/25; A61L 2202/16; A61L 2202/12; A61L 2202/11
See application file for complete search history.

(56) References Cited

U.S. PATENT DOCUMENTS

| | | | | |
|---|---|---|---|---|
| 9,095,633 | B1* | 8/2015 | Dayton | A61L 2/10 |
| 9,144,618 | B2* | 9/2015 | Kreitenberg | A61L 2/10 |
| 9,149,549 | B2* | 10/2015 | Kreitenberg | B64D 11/0007 |
| 10,195,298 | B2* | 2/2019 | Kreitenberg | A61L 2/26 |
| 10,300,157 | B2* | 5/2019 | Jones | B62B 3/14 |
| 10,406,253 | B2* | 9/2019 | Kreitenberg | A61L 2/10 |
| 10,500,296 | B2* | 12/2019 | Kreitenberg | A61L 9/20 |
| 2011/0256019 | A1 | 10/2011 | Gruen et al. | |
| 2012/0248332 | A1* | 10/2012 | Kreitenberg | A61L 2/10 250/455.11 |
| 2014/0059796 | A1 | 3/2014 | Boodaghians et al. | |
| 2014/0241941 | A1 | 8/2014 | Kreitenberg | |
| 2015/0203005 | A1* | 7/2015 | Pendlebury | B60N 3/102 297/188.14 |
| 2015/0209459 | A1* | 7/2015 | Kreitenberg | A61L 2/10 250/492.1 |
| 2015/0359921 | A1* | 12/2015 | Palmer | A61L 2/00 422/4 |
| 2015/0367008 | A1* | 12/2015 | Romo | A61L 2/24 422/24 |
| 2018/0178823 | A1* | 6/2018 | Yang | A61L 2/10 |

OTHER PUBLICATIONS

Extended European Search Report, dated May 19, 2020, from related European Patent App. No. 18763642.8.
Nemko Report No. RJ6731-PT, Performance Testing Letter Report, Dec. 21, 2018.

* cited by examiner

OPERATOR SHIELDED MANUALLY TRANSPORTABLE ULTRAVIOLET DISINFECTION CART

RELATED APPLICATION

This application claims priority from the U.S. provisional patent application Ser. No. 62/469,930 filed Mar. 10, 2017 and entitled "Operator Shielded Manually Transportable Ultraviolet Disinfection Cart."

BACKGROUND

Ultraviolet "C" (UVC) and similar wavelengths of light have known and useful germicidal properties. Platforms and carts emitting UVC have been used to sanitize surfaces in healthcare, transportation, theatres and other environments where people, and the germs they carry, congregate, assemble and transit.

Human exposure to UVC may cause eye and skin irritation at higher doses. To avoid human UVC exposure, platforms have been stationary with various timing, UVC metering, alarms and shutoffs to prevent exposure. The area to be sanitized must be devoid of personnel.

There are technical advantages, such as more uniform surface exposure, to emitters that move about the area to be sanitized. Autonomously driving robots can accomplish this without human exposure. Such emitters include patents awarded to this applicant. Current and foreseeable robotic constraints limit the practical use of robotic sensing, navigating, actuation and UVC powering of such emitters.

Therefore, it is highly desirable and useful to provide a transportable platform that is "drivable" by a person with specific safety features that prevent sensitive eye and skin UVC exposure. This disclosure permits an operator to safely perform sensing, navigation, actuation and UVC powering of a variety of UVC emitters. Personal protective gear, including clothing, glasses, hoods and face shields may be used, but are optional.

SUMMARY

This disclosure utilizes a variety of shielding structures and strategies to allow an operator to transport and manipulate an ultraviolet emitting platform/cart safely without skin and eye exposure.

The present disclosure generally relates to a sanitation device for sanitizing surfaces. In accordance with one embodiment of the disclosure, the sanitization device includes a mobile body and a source of UV radiation. The source of UV radiation is mounted to the mobile body, which is configured to travel over a surface. The source of UV radiation is configured to direct UV radiation to the surface at a dosage sufficient to diminish microbial loads to acceptable levels. Some distinguishing features of the current disclosure include several features.

A trolley for negotiating aircraft or similar aisles.

Two arms, that are laden with UVC sources are situated to disperse in a plurality of directions. They are articulated to be laterally extensible over the seat backs and retractable within the trolley footprint. They are motor controlled and actuated, and are variably extensible, depending upon the seating configuration. The arms are programmable, depending upon the seating configuration, and they are able to function independent of each other.

One utility of this disclosure is self-evident on an intermittent basis in commercial domestic and international routine travel. In the extreme case of a bioterror threat of dispersing particularly lethal microbes via aircraft, this disclosure has the potential of preventing mass casualties.

The current disclosure provides a rapid, safe and effective means of sanitizing the cabin interior by exposure to germicidal UV-C light during routine ground fueling, and maintenance.

Additional and further objects, features, and advantages of the present disclosure will be readily apparent to those skilled in the art.

Other features and benefits that characterize embodiments of the present disclosure will be apparent upon reading the following detailed description and review of the associated drawings.

DRAWINGS

DESCRIPTION

Figure 1:
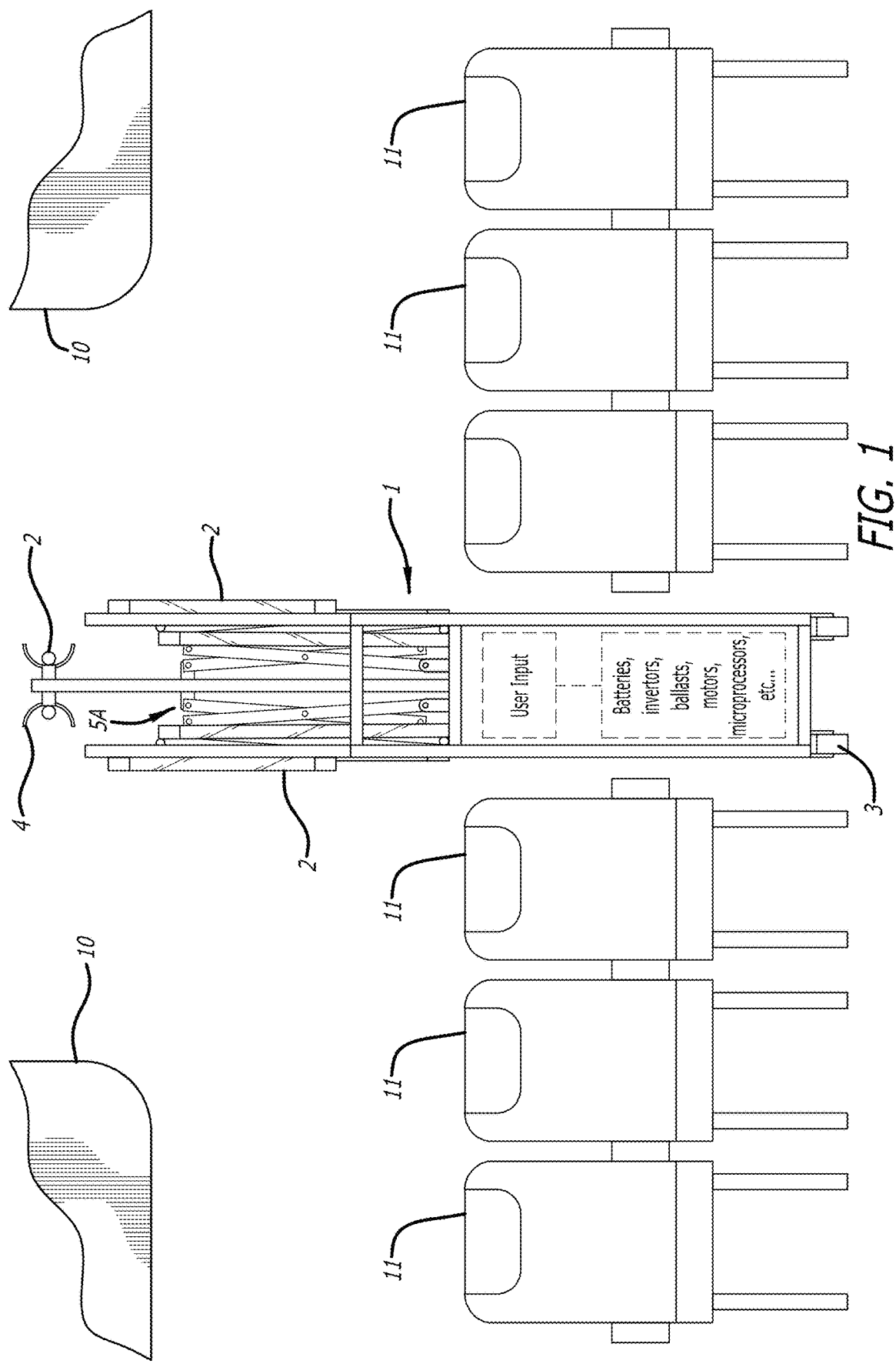
FIG. 1 is a rear view of sanitizing cart with arms folded negotiating the aisle between rows of seats.
Figure 2:
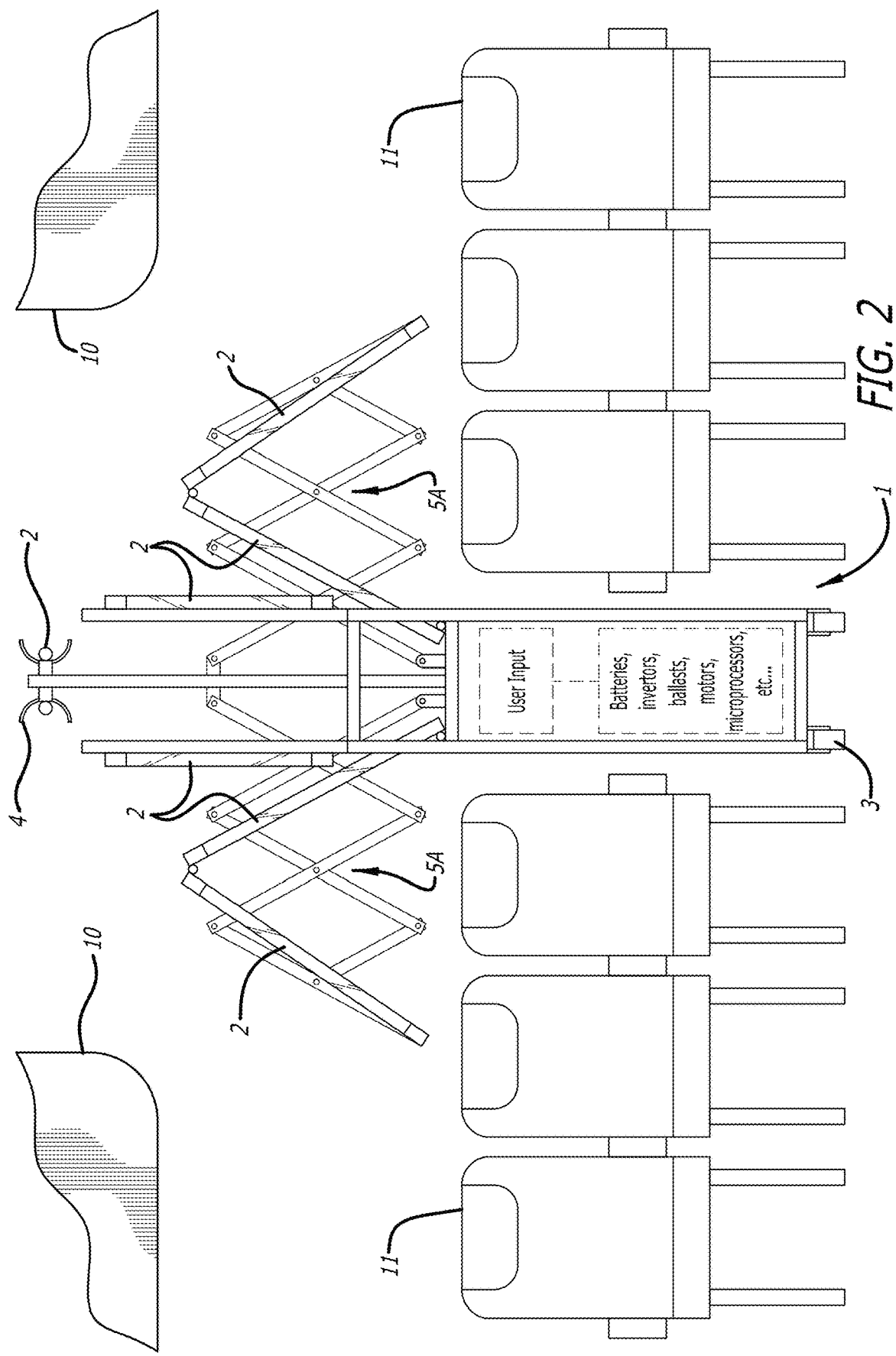
FIG. 2 is a rear view of sanitizing cart with arms unfolded in a first position negotiating the aisle between rows of seats.
Figure 3:
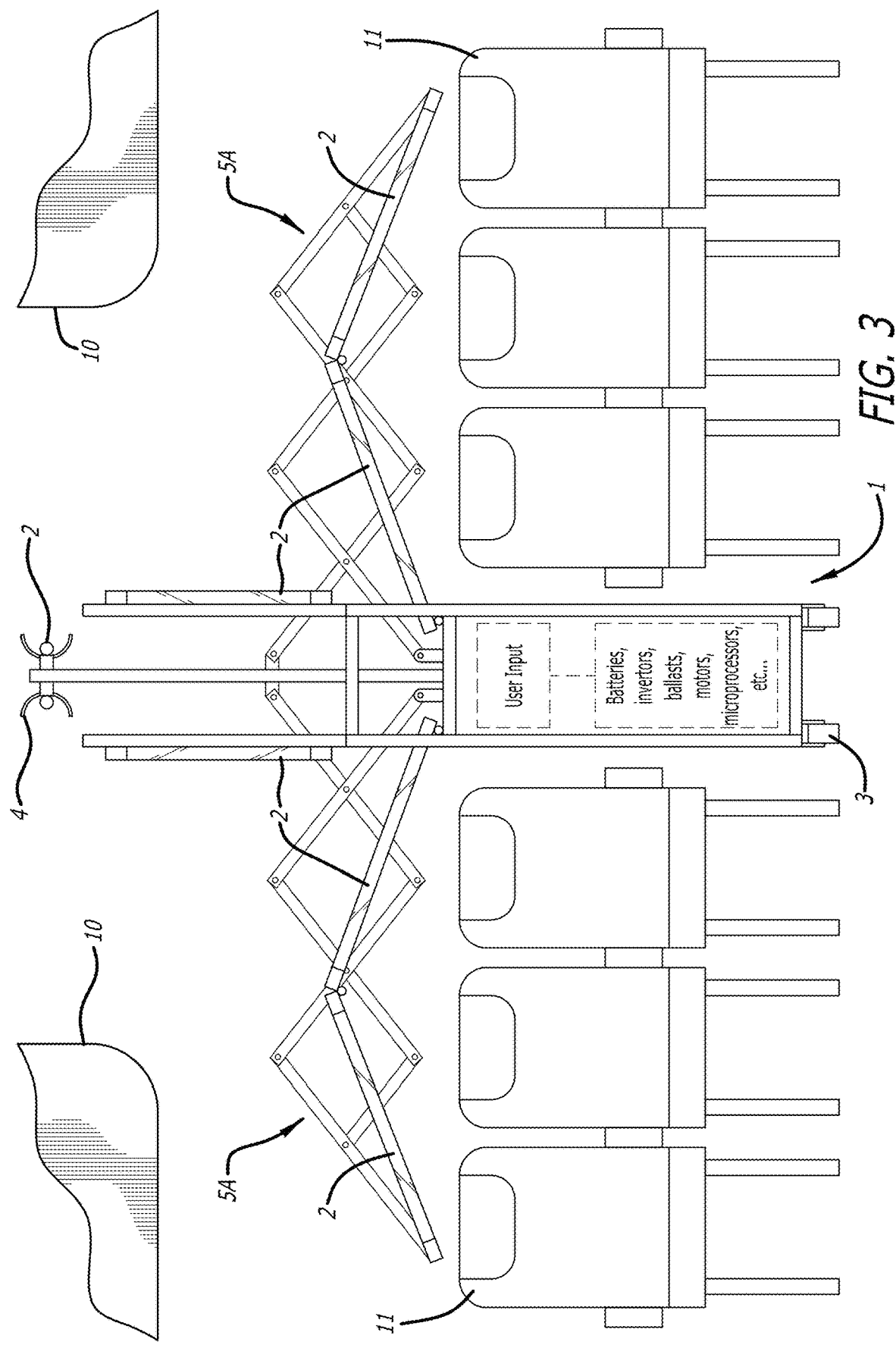
FIG. 3 is a rear view of sanitizing cart with arms unfolded in a second position negotiating the aisle between rows of seats.
Figure 4:
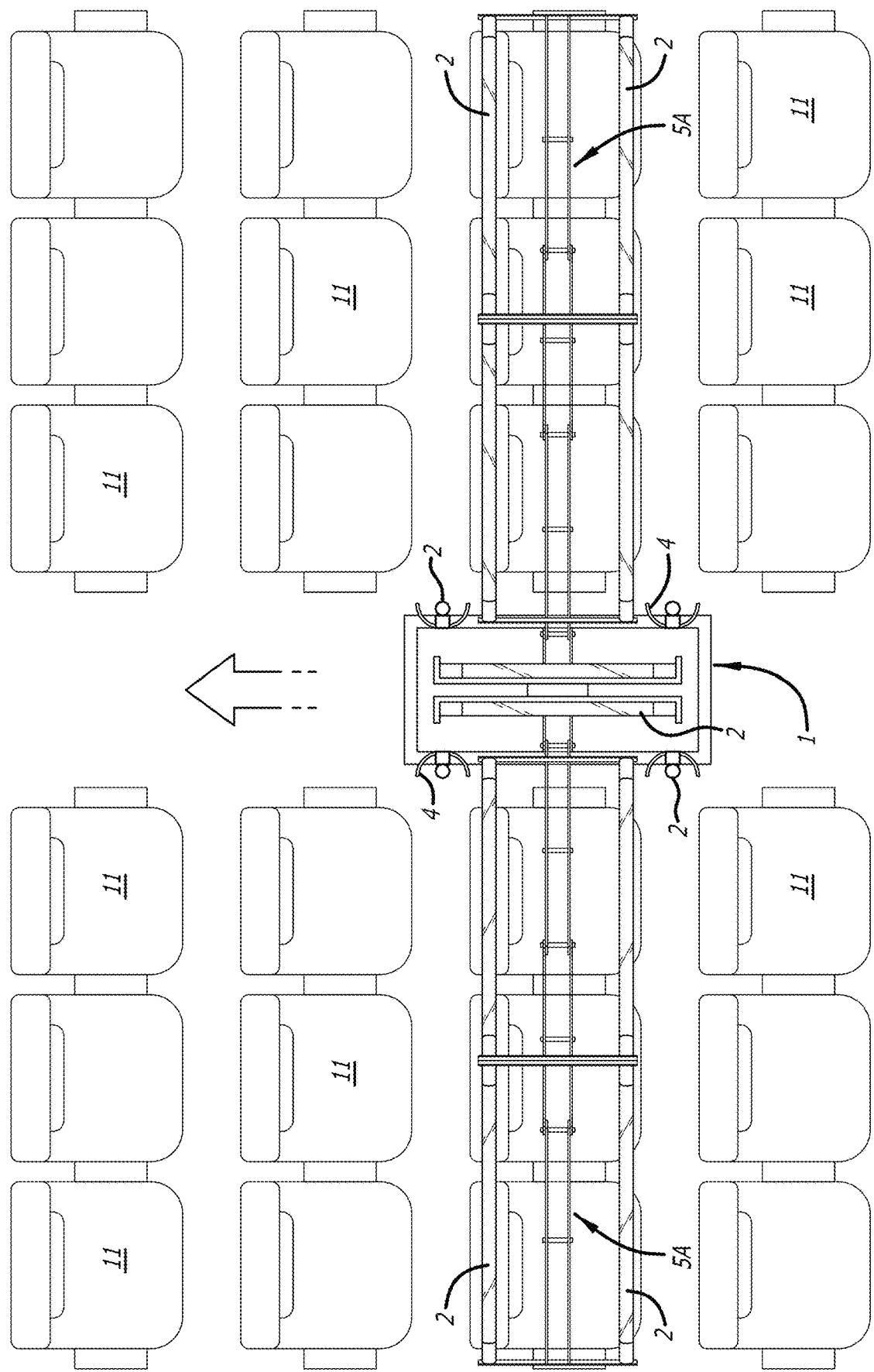
FIG. 4 is a top view of sanitizing cart with arms unfolded in a second position negotiating the aisle between rows of seats.
Figure 5:
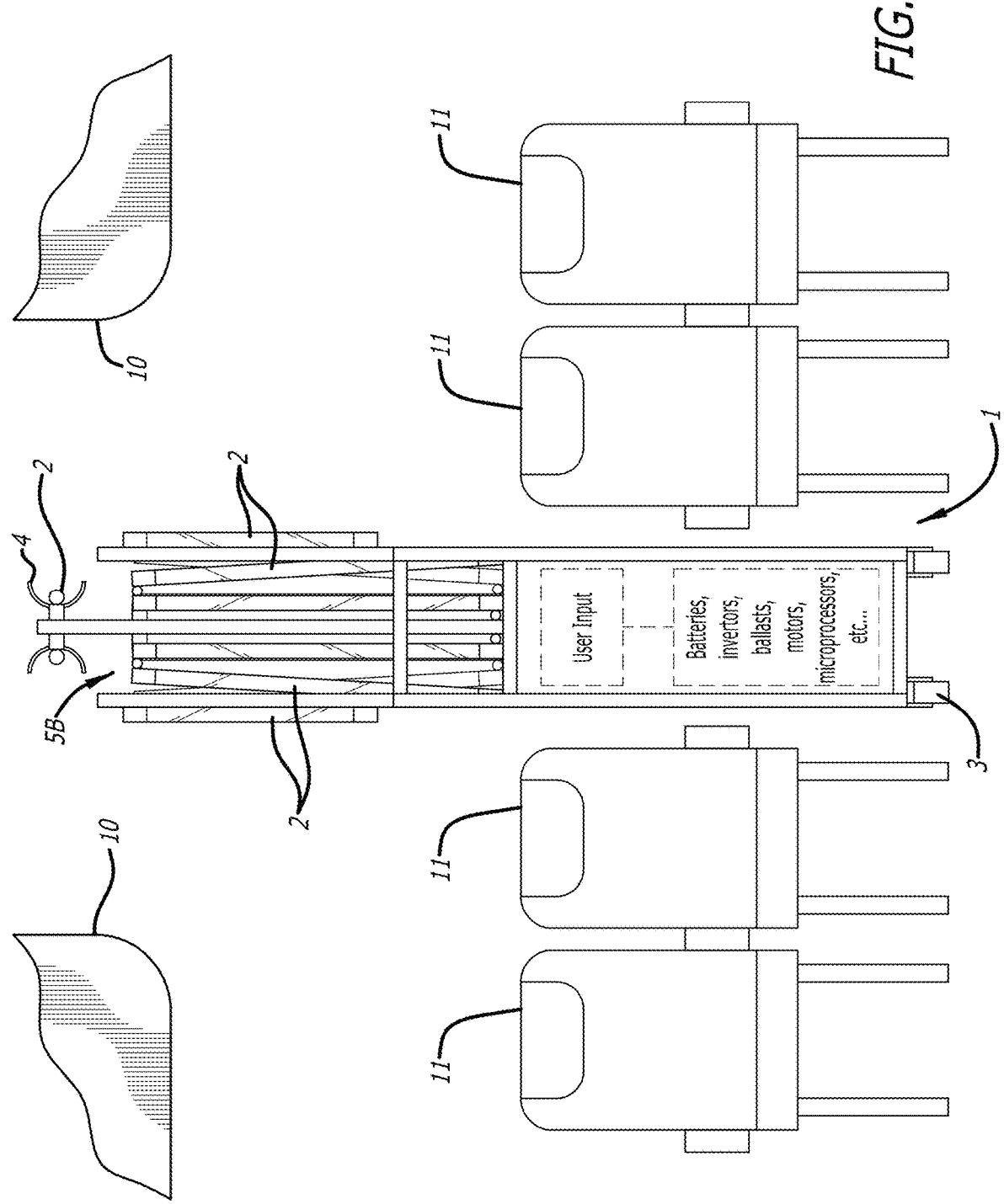
FIG. 5 is a different embodiment rear view of sanitizing cart with arms folded negotiating the aisle between rows of seats.
Figure 6:
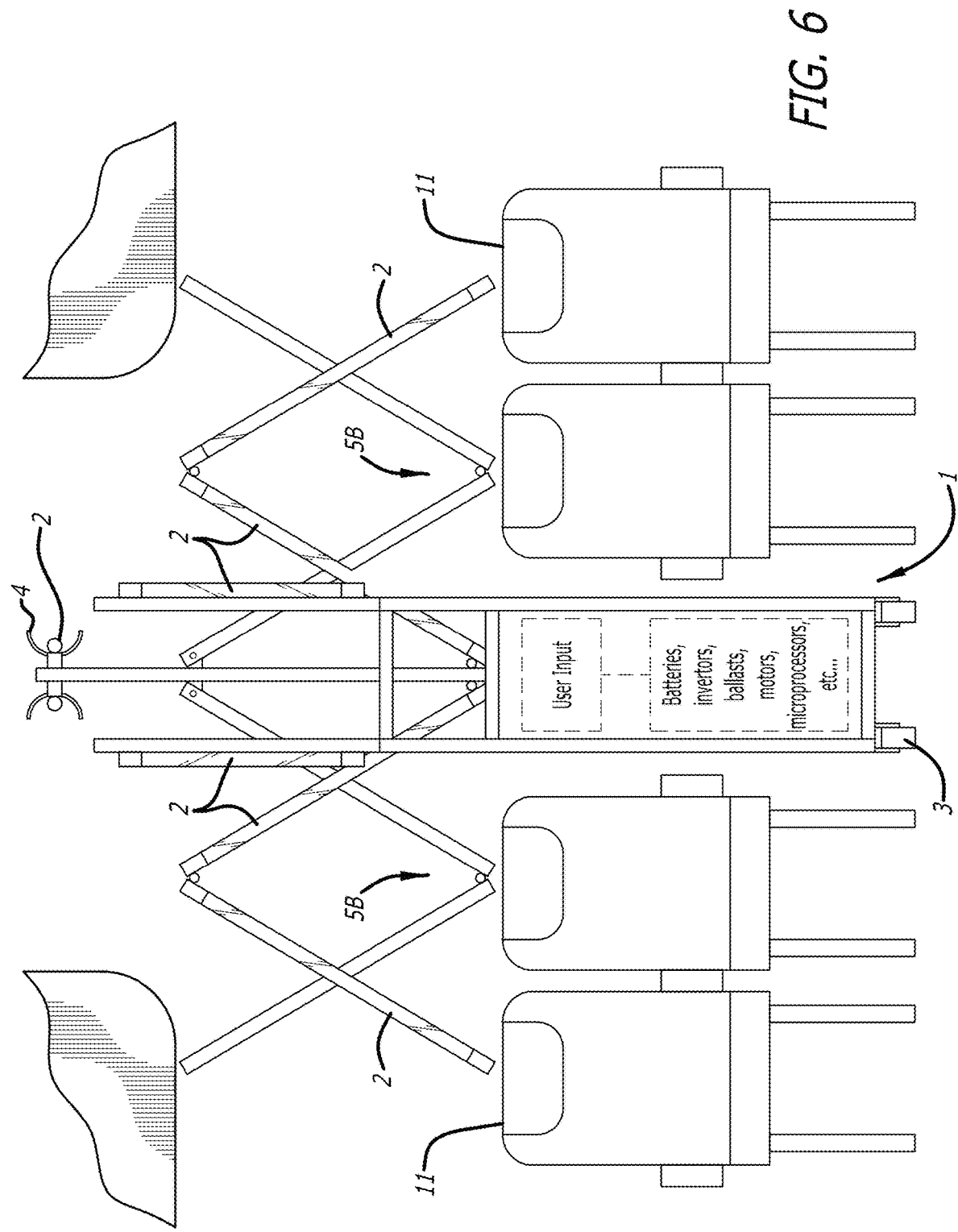
FIG. 6 is a different embodiment rear view of sanitizing cart with arms unfolded in a first position negotiating the aisle between rows of seats.
Figure 7:
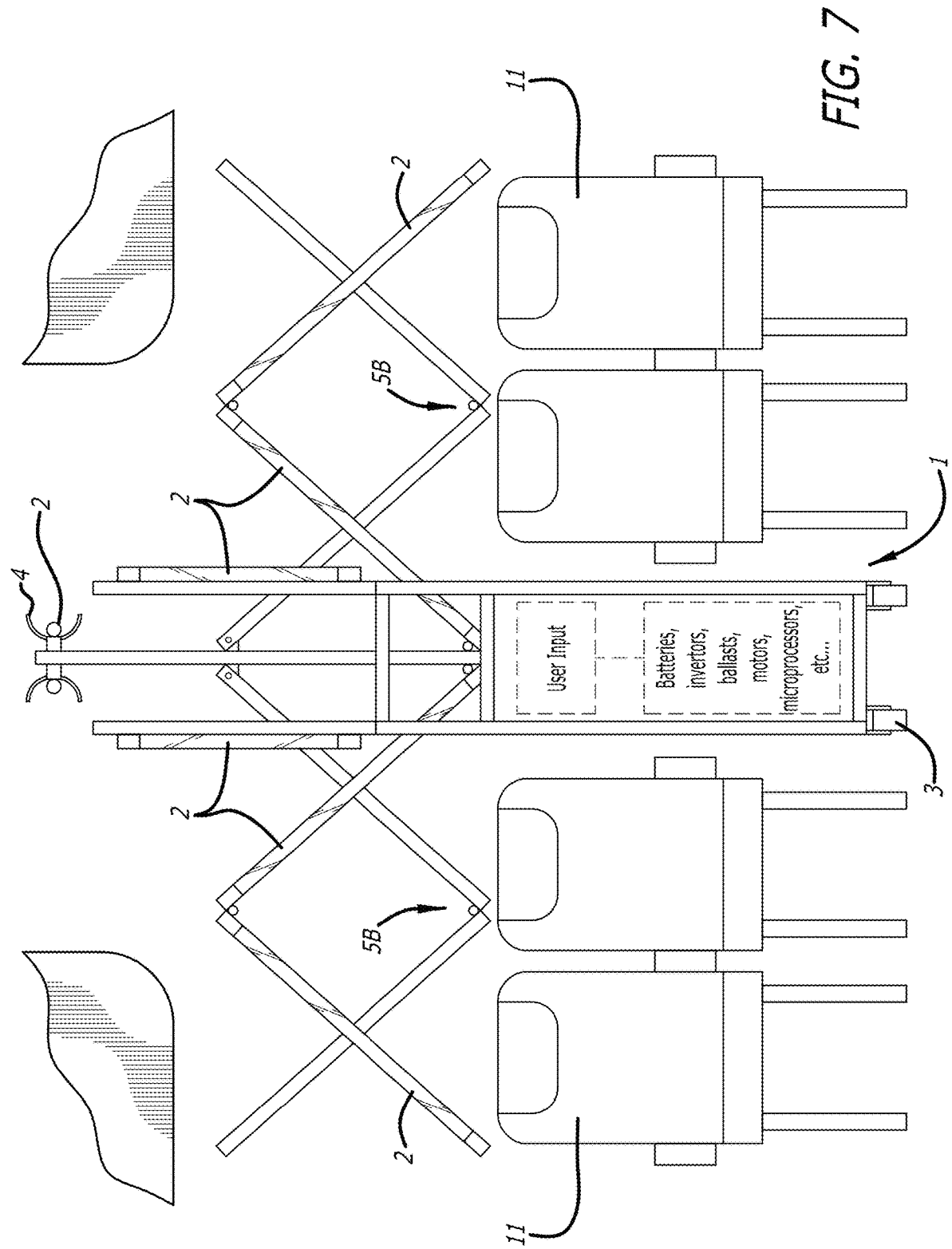
FIG. 7 is a different embodiment rear view of sanitizing cart with arms unfolded in a second position negotiating the aisle between rows of seats.
Figure 8:
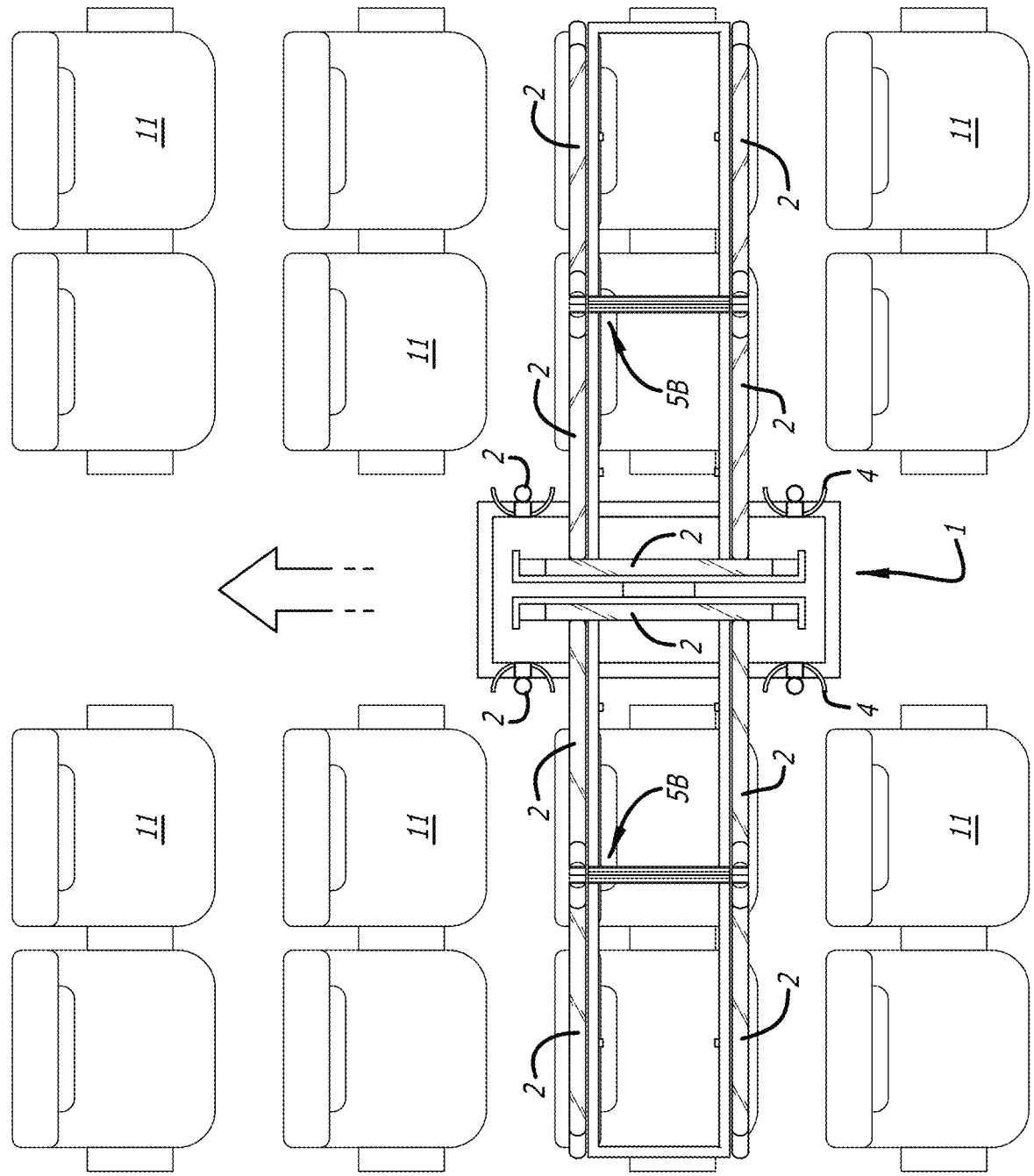
FIG. 8 is a different embodiment top view of sanitizing cart with arms unfolded in a second position negotiating the aisle between rows of seats.
Figure 9:
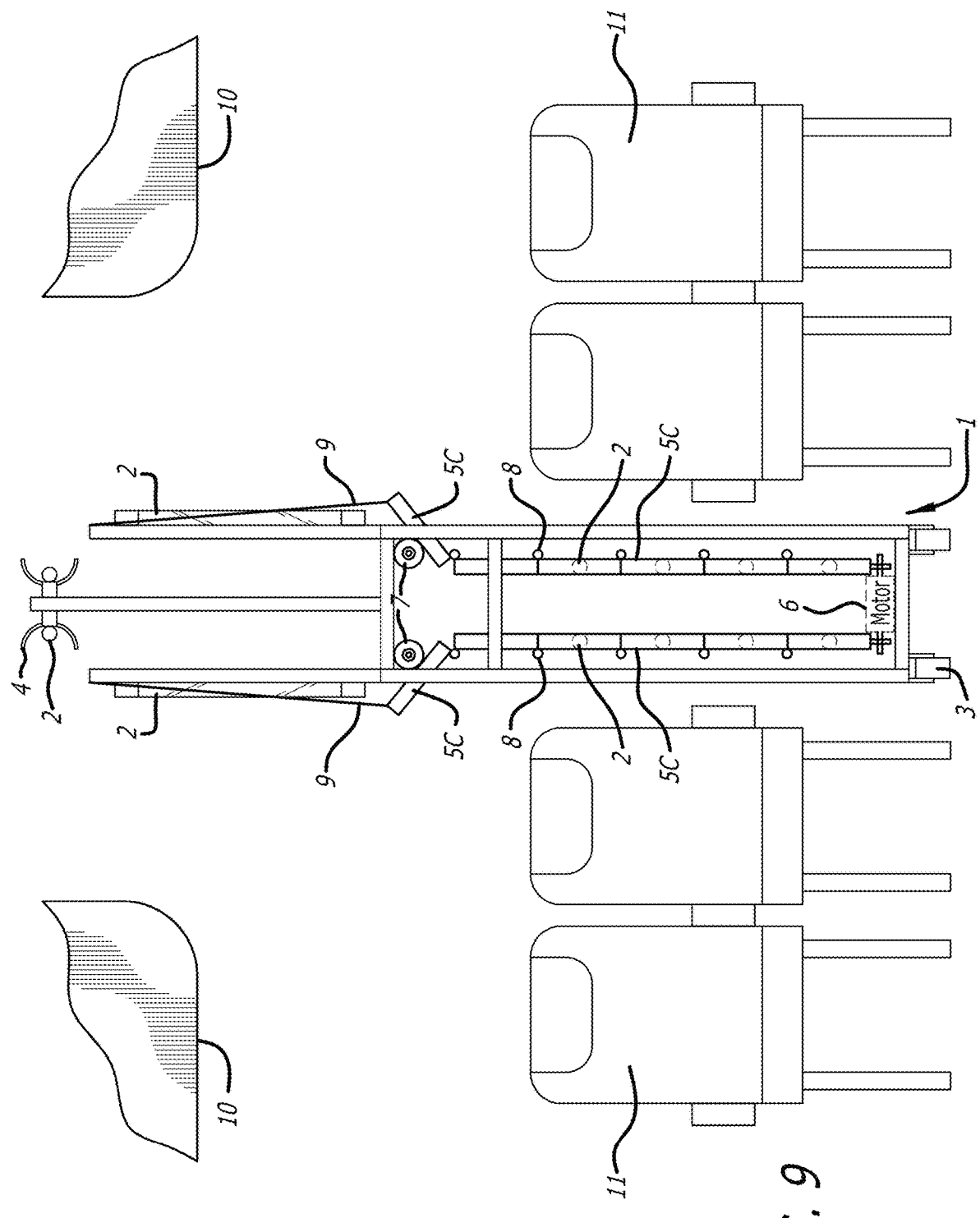
FIG. 9 is a different embodiment rear view of sanitizing cart with arms folded negotiating the aisle between rows of seats.
Figure 10:
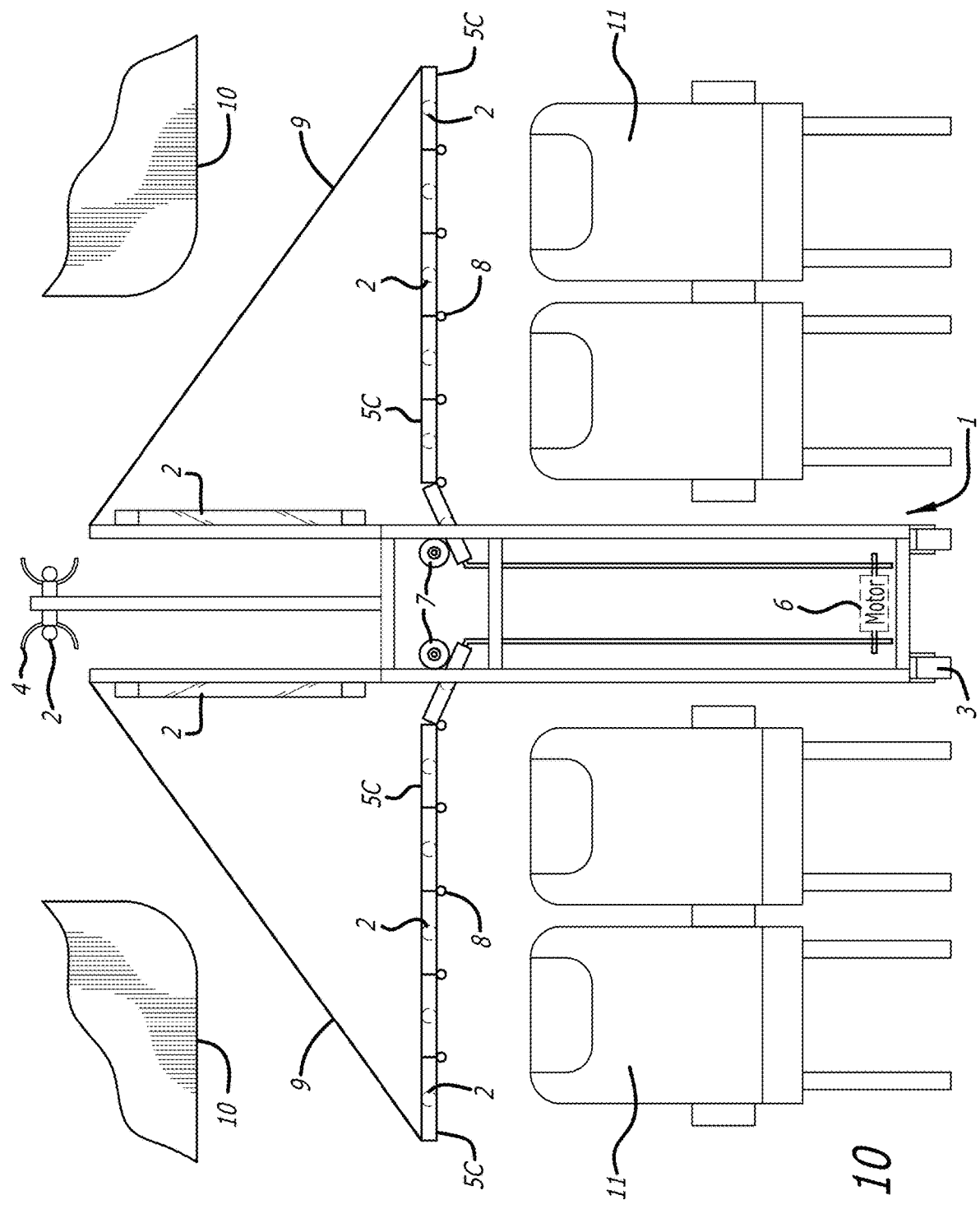
FIG. 10 is a different embodiment rear view of sanitizing cart with arms unfolded in a first position negotiating the aisle between rows of seats.
Figure 11:
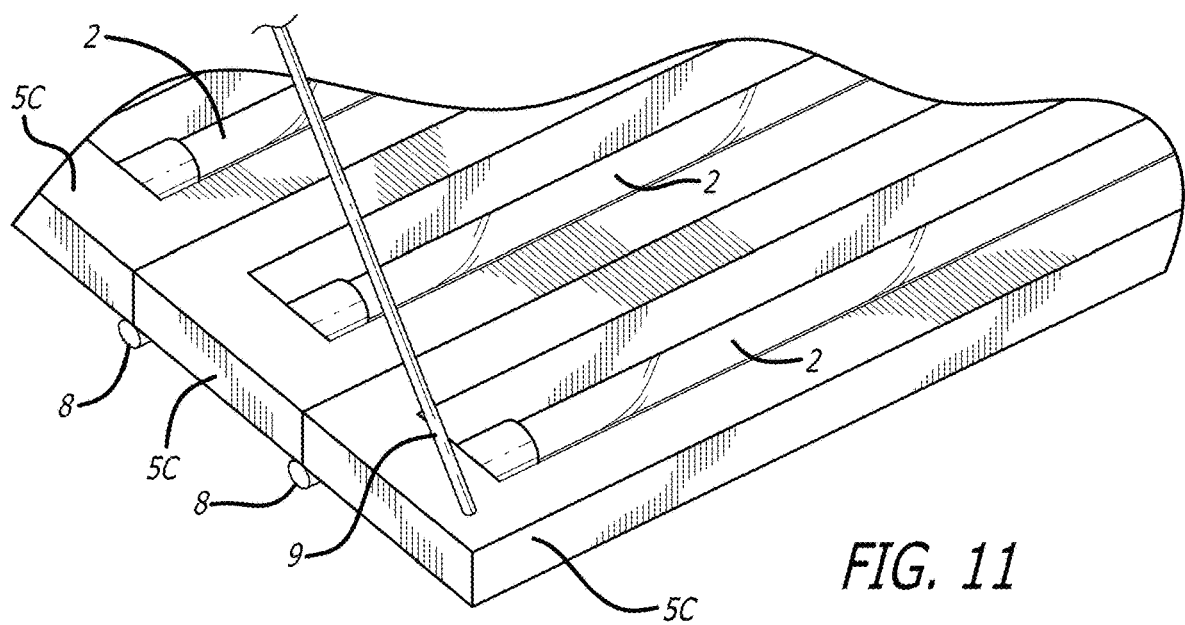
FIG. 11 is perspective view of part of the UV tubes in the arm housing.
Figure 12:
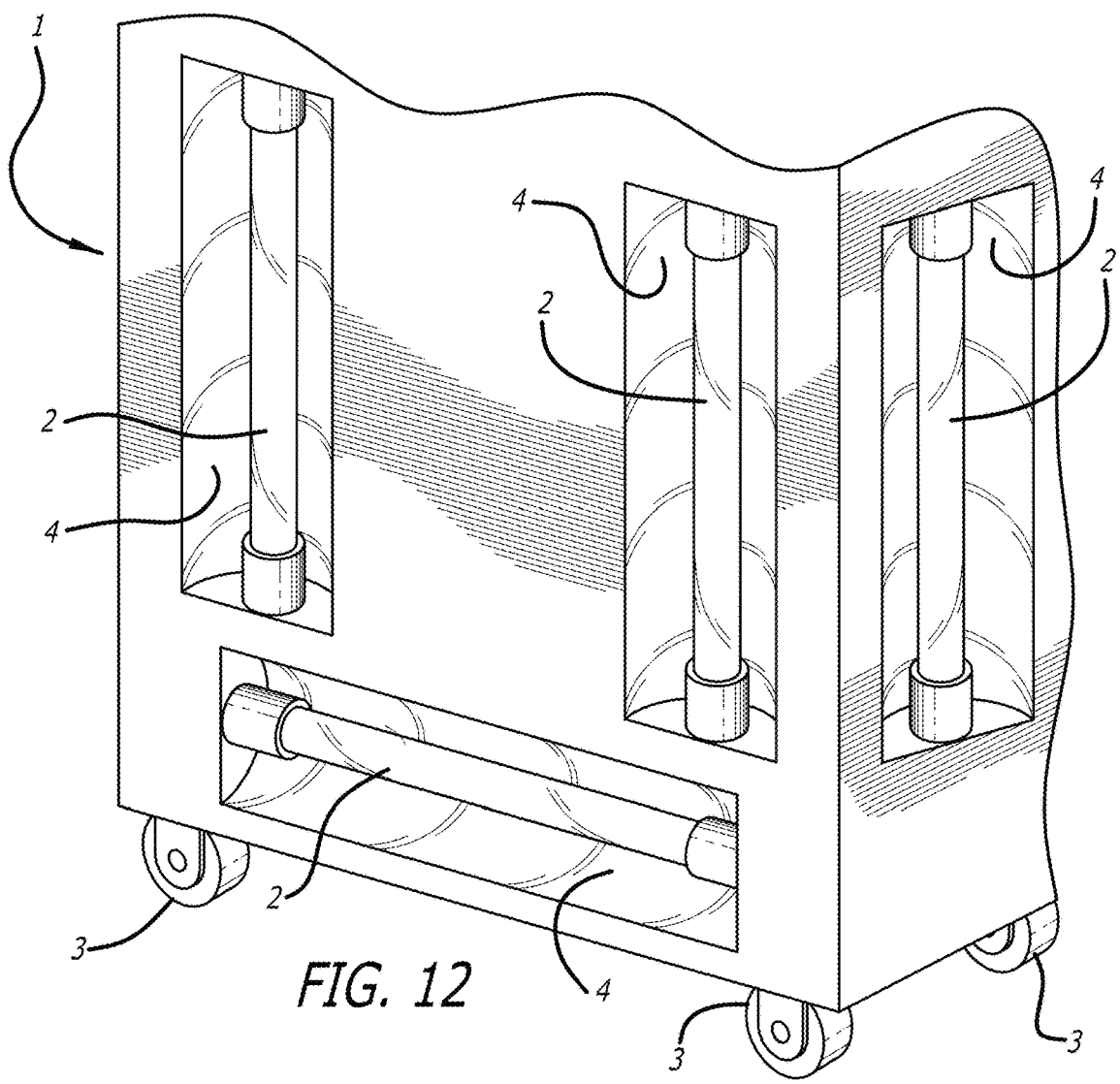
FIG. 12 is perspective view of part of the UV tubes in the trolley.
Figure 13:
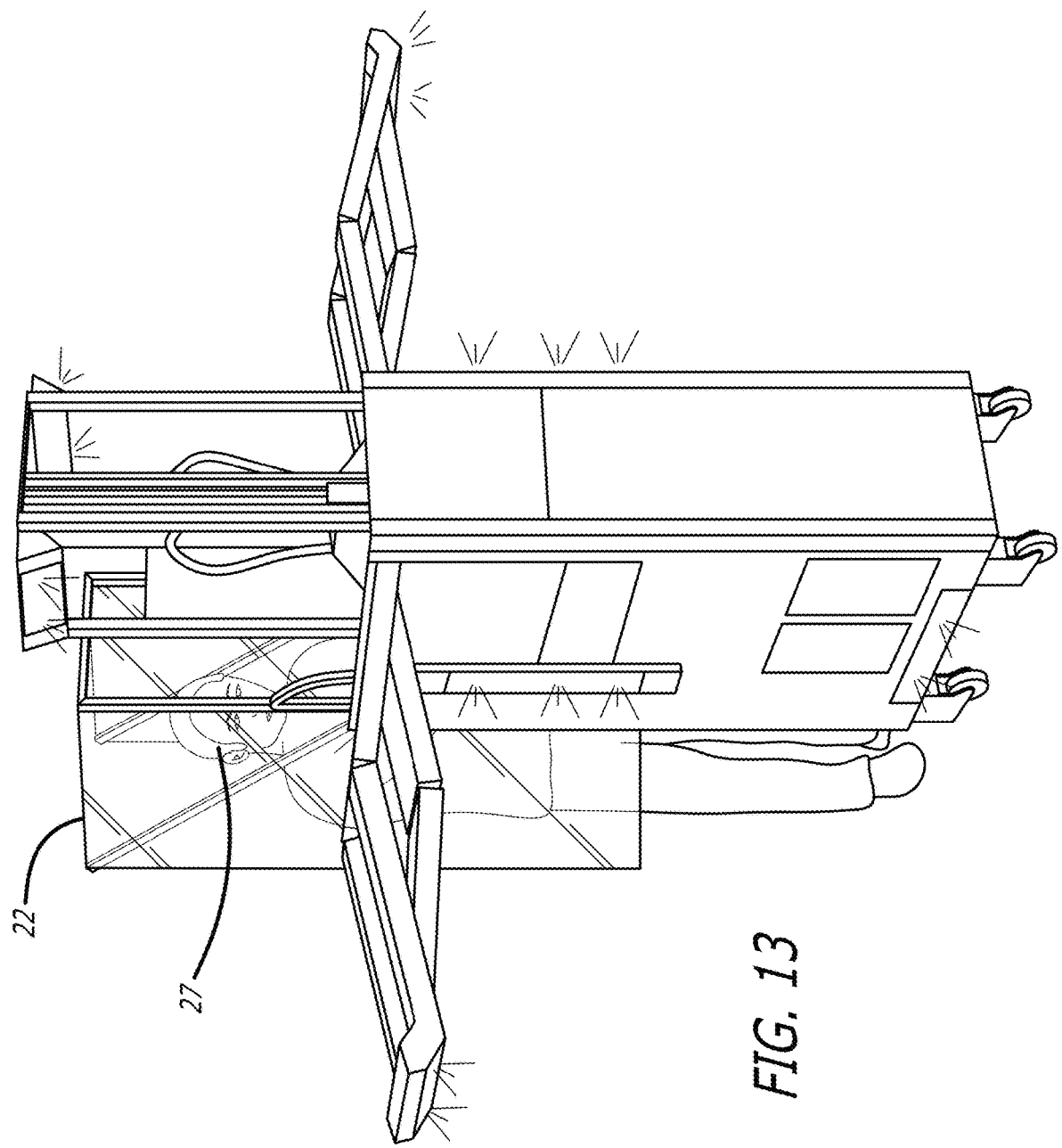
FIG. 13 is perspective view of trolley with the UV tubes and an extended protective shield.
Figure 14:
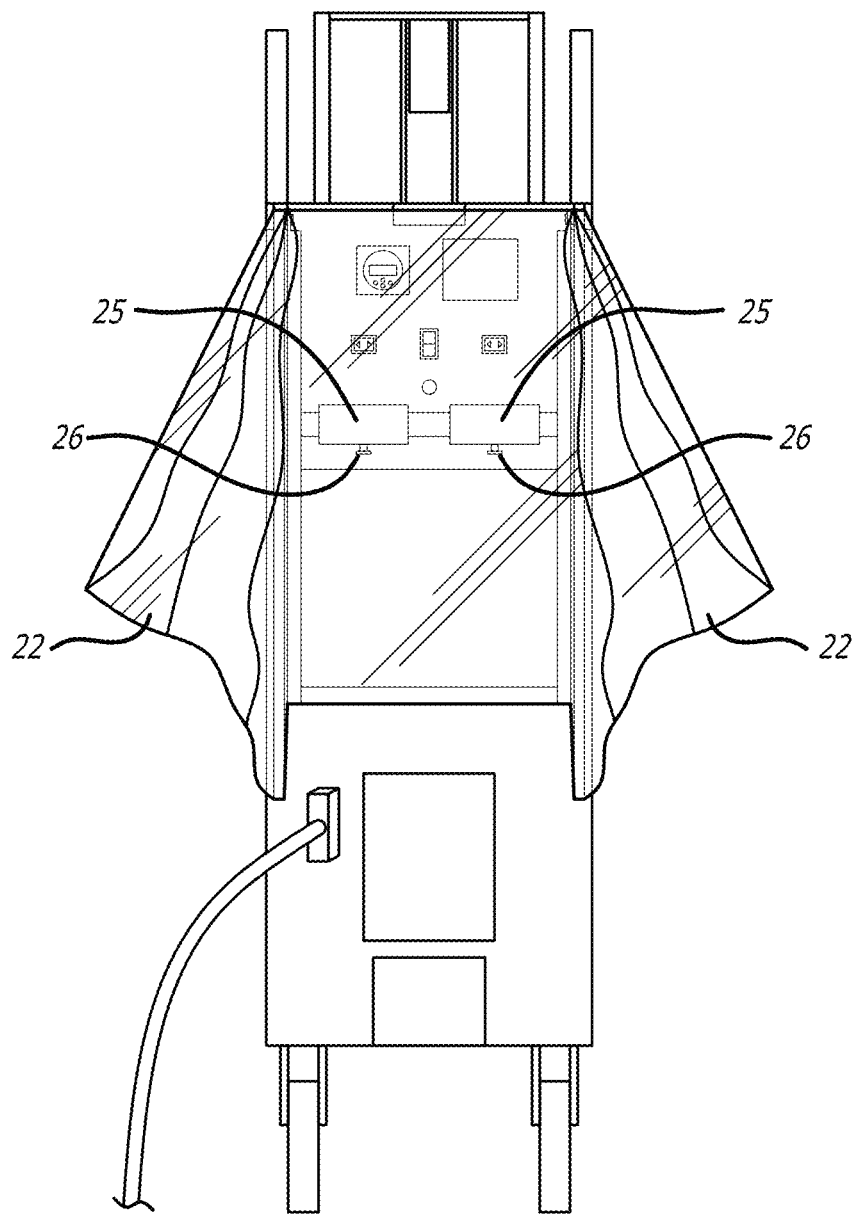
FIG. 14 is rear view of trolley with the collapsed protective shield.
Figure 15:
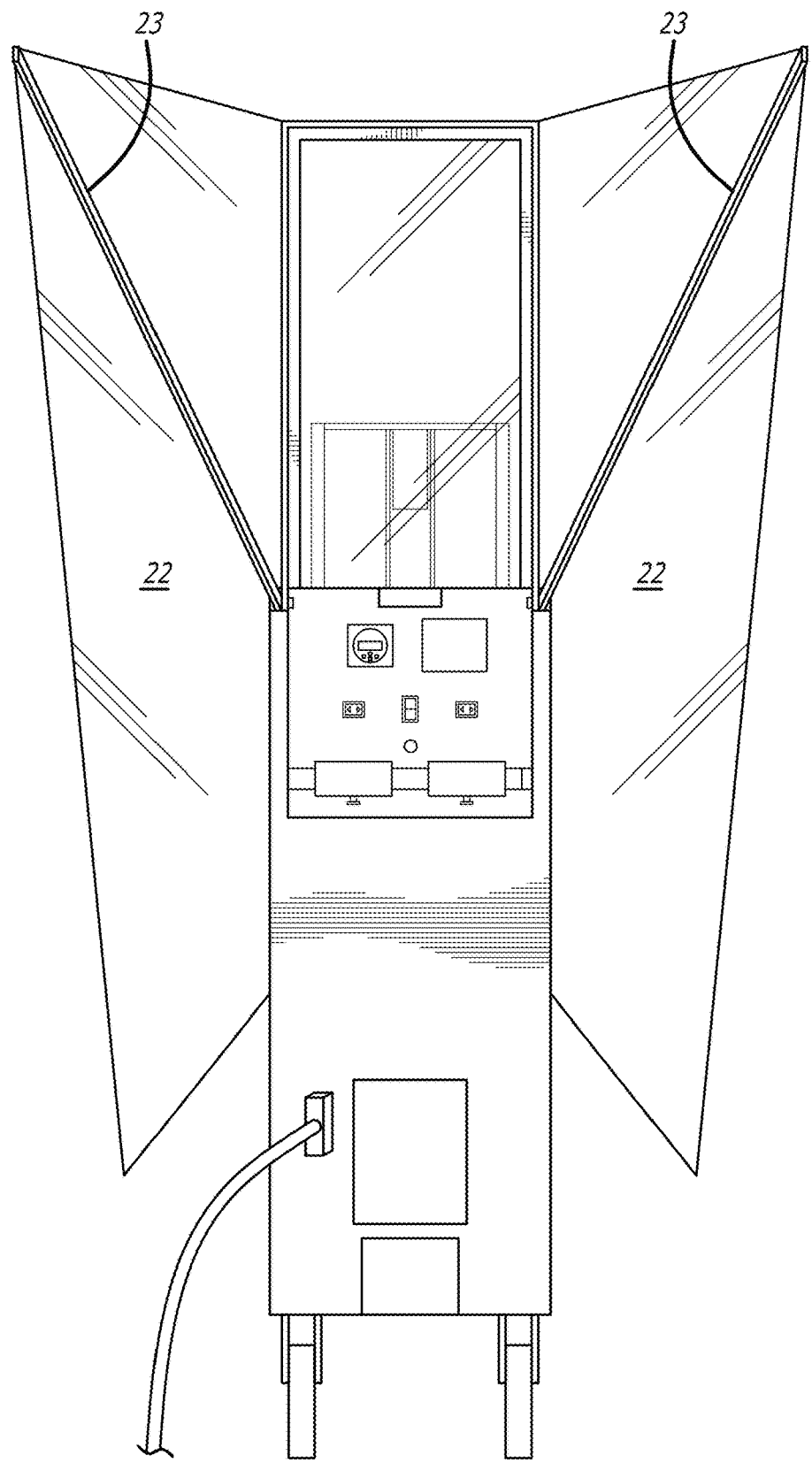
FIG. 15 is rear view of trolley with the extended protective shield.
Figure 16C:
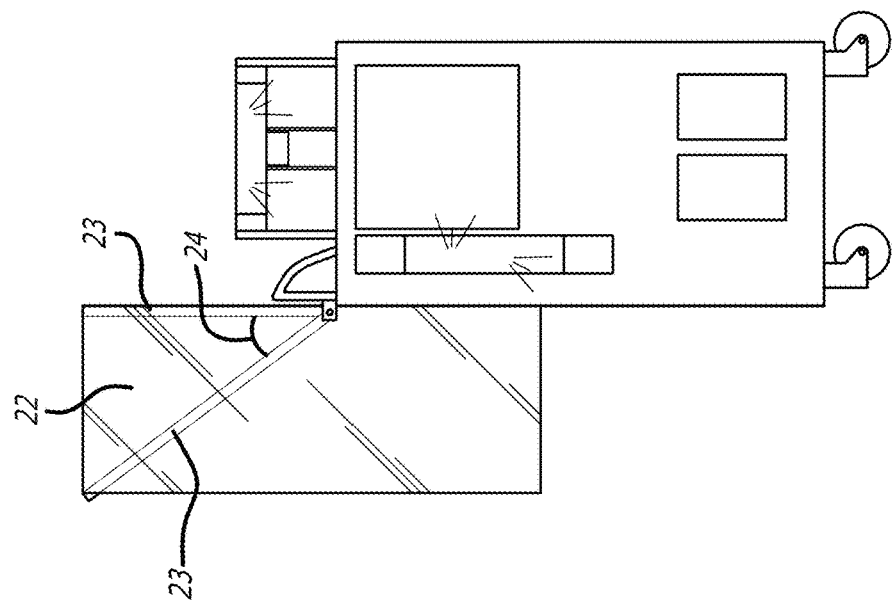
FIG. 16C is side view of trolley with the fully unfolded protective shield.
Figure 16B:
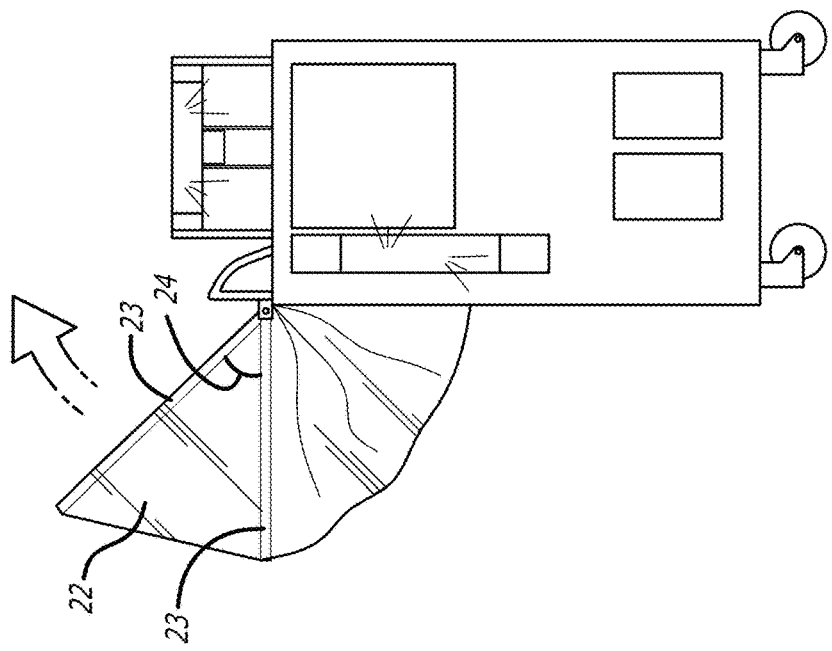
FIG. 16B is side view of trolley with the partly unfolded protective shield.
Figure 16A:
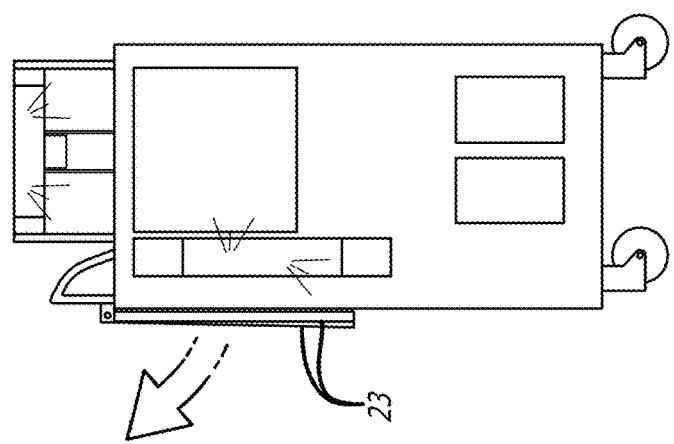
FIG. 16A is side view of trolley with the folded protective shield.
Figure 17:
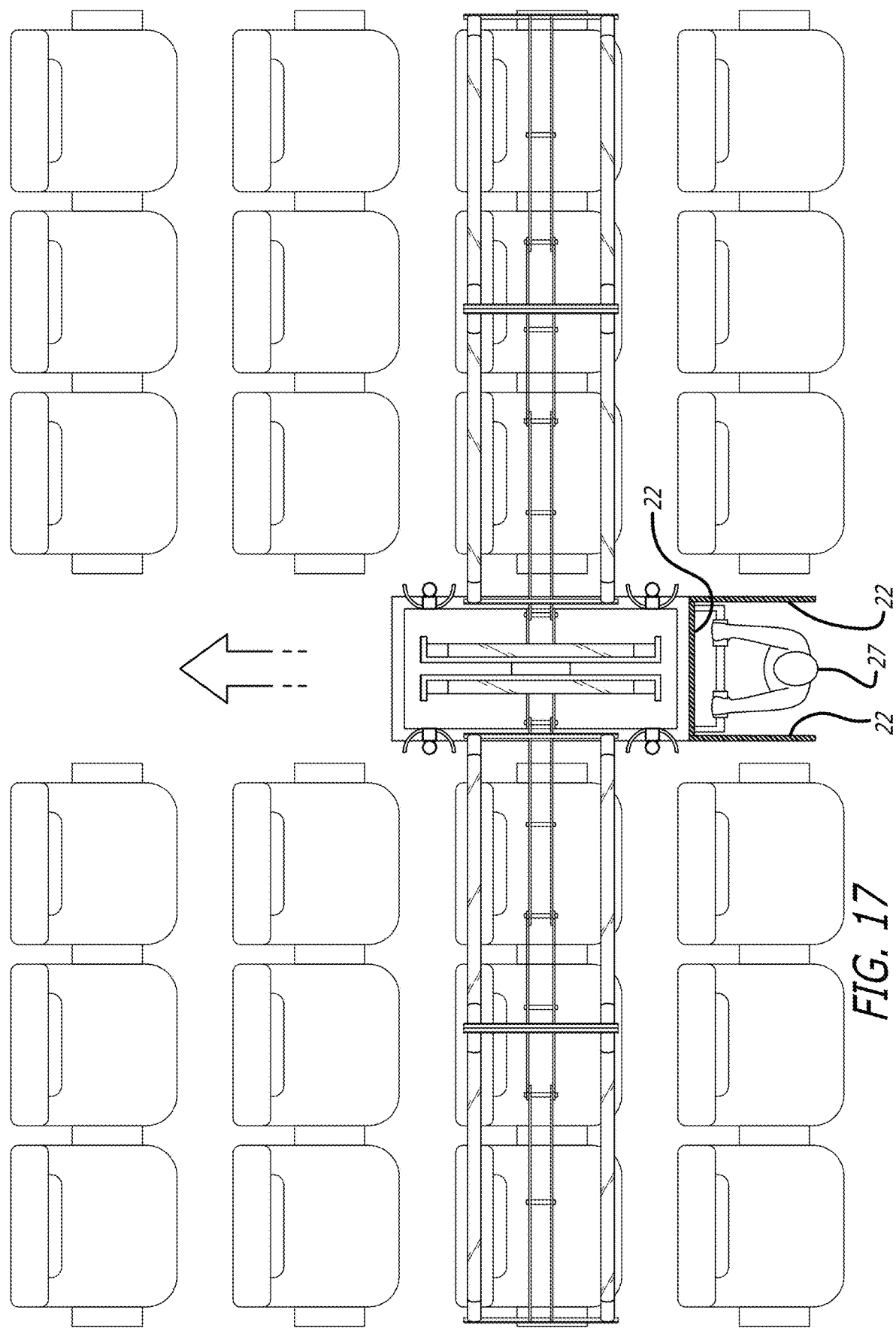
FIG. 17 is a top view of sanitizing cart with arms unfolded negotiating the aisle between rows of seats and the unfolded protective shield about the user.

A system, device and method of shielding comprises a structure, components and methodology to allow a person to operate a UVC emitting cart without personal UVC exposure for sanitizing a surface, the surface optionally being an inside an aircraft cabin.

There is a mobile body configured to travel over a surface; and a source of UV radiation mounted to the mobile body and configured to direct UV radiation to the surface at a predetermined dosage. At least two articulated arms are mounted to the mobile body, and there are UV lamps mounted respectively on the arms.

The mobile body is a trolley or cart for negotiating an area optionally an aircraft aisle, A power source for activating the UV radiation as the trolley or cart moves along an area optionally the aircraft aisle. The two articulated arms are mounted with the mobile body and extendable from the mobile body at a position movable an area optionally n over the seats and the UV lamps are directed to an area optionally the seat surface. When extended from the mobile body and back into mobile body they optionally above seat level. Selectively the multiple UV lamps are set up in end to end relationship, and selectively the arms for the lamps are selectively foldable inwardly relative to each other and towards the trolley and outwardly from each other and from the trolley to extend selectively over the seats; structure, components.

There is at least one of a UVC protective shield, the shield selectively providing a multisided enclosure that selectively envelopes and/or separates the operator from the UVC in the surrounding environment.

The description shows the features of the current disclosure on the inventor's Ultraviolet Autonomous Trolleys (U.S. Patent #'s 8,907,304, 8,999,238, 9,144,618 & 9,149,549) for convenience, but is similarly applicable to any UVC emitting device. The contents of those patents are incorporated by reference in their entirety.

The UVC emitting cart is manually maneuverable with handles and wheels that permit navigation in a wide variety of environments. There is a control panel that gives feedback to the operator including speed, battery status, UVC output, alarms, etc. There are switches, dials and other appropriate controls to position and power UVC sources, navigate the cart, and operate ancillary equipment such as fans.

An element of the current disclosure takes advantage of the physical distinctions between light in the visible and light in the ultraviolet spectrums. Light in the visible spectrum can be transmitted readily through a variety of materials including glass, plastics, vinyls and other polymers that to the human eye appear transparent. However, many of these same materials are impenetrable to light in the ultraviolet spectrum, particularly UVC. Shields constructed of such materials allow the operator to use visual feedback to navigate and manipulate the UVC emitting cart, while providing protection from UVC exposure of eyes and skin.

In one embodiment of such a UVC protective shield 22 is shown in the accompanying figures. The shield provides a multisided enclosure that envelopes and separates the operator 27 from the UVC in the surrounding environment.

The shield 22 may be permanent and made of rigid materials or collapsible in a variety of known mechanisms to allow stowage into a smaller volume. Such mechanisms include but are not limited to flexible and bendable materials such as vinyls, or mechanisms that include foldable, nesting, telescoping, rotating, sliding and similar strategies. Combinations of these mechanisms are also covered and are shown in the embodiment.

When in the stowed position covers and provides a physical barrier to the control panel to permit UVC activation only when the shield is in the deployed position. Similarly, interlock switches, proximity sensor switches or similar devices can be provided to ensure UVC powering only when the shield is deployed.

An additional feature shows a pair of spars 23 that pivot at angled axes 24. When stowed, the distance between the spars is narrowed corresponding to a narrow cart footprint. When the shield 22 is deployed, the distance between the spars 23 is wide to comfortably contain the operator's body width.

As additional safety feature, the handles 25 used to navigate the cart are within the shield. Momentary power switches 26 are embedded within the handles. This arrangement requires the operator to be within the shield to power the UVC sources. If the operator attempts to leave the confines of the shield, the UVC immediately shuts down.

The present disclosure generally relates to a sanitization device that utilizes a source of UV radiation to provide a means for sanitizing a surface. As will be discussed below in greater detail, embodiments of the sanitization device include a source of UV radiation in combination with a mobile body, or a housing for handheld operation. Additional embodiments of the present disclosure relate to methods of sanitizing surfaces using the sanitization devices of the present disclosure.

In accordance with another embodiment of the disclosure, the sanitization device includes a mobile body, a surface cleaning component, and a source of UV radiation. The surface cleaning component and the source of UV radiation are mounted to the mobile body, which is configured to travel over a surface. The surface cleaning component is configured to engage the surface and the source of UV radiation is configured to direct UV radiation to the surface.

In accordance with yet another embodiment of the disclosure, the sanitization device includes a housing, a source of UV radiation, and a sensor. The source of UV radiation is contained in the housing and positioned to transmit UV radiation through an opening in the housing. The sensor is configured to detect when the source is within a predetermined distance from a surface to be sanitized.

Additional embodiments of the present disclosure are directed to methods of using the above-identified sanitization devices to sanitize a surface.

A sanitization device for sanitizing a surface inside an area optionally an aircraft cabin comprises a mobile body configured to travel over a surface. There is a source of UV radiation mounted to the mobile body and configured to direct UV radiation to the surface at a predetermined dosage. There are at least two articulated arms mounted to the mobile body, and UV lamps are mounted respectively on the arms. The mobile body is a trolley or cart for negotiating an area optionally an aircraft aisle.

In another form there is a sanitization device for sanitizing a surface an area optionally inside an aircraft cabin. There is a mobile body configured to travel over a surface; and a source of UV radiation mounted to the mobile body and configured to direct UV radiation to the surface at a predetermined dosage. At least one arm is mounted to the mobile body, and a UV lamp is mounted on the arm. The mobile body is a trolley or cart for negotiating an aircraft aisle.

The arm is movable from a position of storage with the mobile body to a position to extend from the mobile body wherein in the extended position the arm is operational to effect sanitization.

In one form each arm being for independent operation.

There are means for controlling motion of the arms an area optionally over and about the aircraft surfaces, such surfaces including seats of the aircraft.

The arms are mounted with the mobile body and extendable from the mobile body at a position an area optionally above the back rest of seats. The arms are movable over the seats and the UV lamps are directed to the seat surface as well as an area optionally above the seats, and an area optionally toward the interior sides of the fuselage.

The arm or arms are mounted with the mobile body and extendable from the mobile body at a position essentially an area optionally solely above seats of an aircraft.

A surface cleaning component can be mounted to the mobile body and configured to engage the surface on which the mobile body travels.

The device includes a self-contained powering unit for powering the UV source.

The device can include a sensor for measuring the distance and or power the UV lamps relative to the surface and controlling the amount of and distance of the lamps from the surface and/or UV energy transmitted to the surface.

There is a method of sanitizing the seat surface an area optionally in an aircraft cabin comprising the following steps. A sanitization device is provided to include a mobile body configured to travel an area optionally along an aisle of an aircraft, and there is step of sanitizing with a device extending from the mobile device extendible an area optionally across the seat surface.

There can be a surface cleaning component mounted to the mobile body and configured to engage the surface, A source of UV radiation mounted to the mobile body is moved so that the sanitization device is directed an area optionally across the seat surface. The seat surface an area optionally is exposed to UV radiation produced by the source, and the mobile body is moved along an aisle while the device travels an area optionally over multiple seat surfaces.

A source of UV radiation mounted to the mobile body is directed an area optionally to the seat surfaces at a predetermined dosage; extending at least one arm mounted to the mobile body with UV lamps mounted on the arm an area optionally over the seats as the mobile body travels an area optionally along an aircraft aisle. The mobile body is powered by a power source on board the mobile device.

The arm or arms are mounted on the mobile body and extend from the mobile body at least an area optionally at a height above the seat level of the seat, and an area optionally preferably between the seat level and the top of the backrest seat. The arms are an area optionally preferably between the top of the backrest and the overhead bins.

A method of sanitizing includes a process wherein as the trolley moves on wheels an area optionally along an aisle of an aircraft cabin, the arm is extended for movement an area optionally in a space between the top of the cabin and above the top of backrest of the seats.

A method of sanitizing includes a process wherein as the trolley moves on wheels progressively an area optionally along an aisle of an aircraft cabin, the arm is extended for movement in a space between the top of the cabin and progressively above the top of backrest of the seats and the seat portions of the seats.

Some different components of the system are set out: 1) Trolley 2) UVC source (lamp) 3) Trolley wheels 4) reflector 5) arm 6) arm extension retraction mechanism 7) rollers 8) hinges 9) guy wire 10) overhead bins 11) aircraft seats.

The trolley (1) has a "footprint" similar to that of a standard food/beverage trolley used on aircraft, but is of substantially greater height. The trolley has wheels (3), at least one of which is connected to a motor and at least one of which has a steering mechanism. The motor and steering mechanism are connected to an on-board microprocessor controller. There are proximity sensors, not illustrated, along the sides, fore and aft surfaces also connected to the controller.

Ultraviolet "C" (UVC) sources (2) are incorporated into all exterior fore, aft and side, and bottom surfaces of the trolley and located in a manner to maximize exposure of the aircraft interior surfaces. Reflectors (4) are utilized to maximize effective UVC output.

UVC laden "arms" (5) are connected to the trolley in such a manner to be variably laterally extensible above the aircraft seats (11) and below the overhead storage bins (10). These arms (5) may be retracted and stowed within the footprint of the trolley (1) for storage and when maneuvering the trolley (1) into position and on/off the aircraft. UVC source lamps (2) are also located in a sufficiently elevated position to expose the overhead storage bins (10).

Arms (5) may be configured in a variety of embodiments. Arms (5) essentially a folding frame containing UVC Sources (2) attached to a scissors like extension/retraction mechanism (6). The extension/retraction mechanism (6) may be attached to a linear actuator, not illustrated, and motor controlled by the microprocessor. In an alternative arm embodiment the UVC Sources (2) are directly embedded within the extension/retraction mechanism (6). There can be a "roll-up" type arm embodiment with UVC sources (2) embedded into the extension/retraction mechanism (6). For clarity of illustration, these arms (5) contain a limited number of UVC sources (2). Many more UVC sources (2) may be desirable depending upon the desired dose of UVC exposure and other constraints.

These multiple embodiments are not intended to be all inclusive, but rather demonstrative of the myriad ways that this disclosure can be constructed.

Vertical extensions with laterally directed UVC sources (2) also expose the overhead bins. The height of these sources may vary, depending upon aircraft configuration.

Fans, not illustrated for clarity, are also attached to the trolley (1) in such a manner to direct air flow into the path of UVC sources to sterilize the air. For example, fans directed laterally toward the floor can circulate air that might otherwise remain relatively stagnant. UVC light also generates ozone from ambient oxygen which helps deodorize the cabin as an additional benefit.

Rechargeable batteries are located within the trolley to power the motor, controller, steering mechanism, fans, arm extension mechanism and UVC sources. Some UVC lamps may also require ballast. These heavier components are preferentially located at the lower portion of the trolley to maximize lateral anti-tip-over stability. A power cord port, not illustrated, allows plug in charging when the trolley is not in use.

Operation

The trolley (1) is stowed off the aircraft, with arms (5) retracted, and plugged into an external power source to charge the on-board batteries. When ready for use, the apparatus of this disclosure is unplugged and wheeled onto the aircraft in a manner similar to known food/beverage trolleys. The trolley is positioned in the aisle between the first row (or last row) of seats. The arms (5) are extended utilizing the extension/retraction (6) mechanism. The UVC sources (2) are powered on with a delay mechanism sufficient to allow personnel to leave the aircraft, or remotely. The trolley (1) proceeds along the aisle, autonomously centered by the lateral proximity sensors and the wheel (3)

steering mechanism. The apparatus of this disclosure proceeds autonomously to the last row (or first row) of seats, detected by the aft proximity sensors or pre-programmed by the number of rows. The trolley (1) stops, reverses direction and proceeds in the opposite direction in the aisle to the starting point.

The trolley (1) speed of travel may be programmed and is dependent upon the UVC source output, distance from UVC source to surface, and desired level of kill rate. Kill rates are dose dependent, measured in Wsec/m2 and specific microbial sensitivities are known. The total treatment duration should conform to other ground turn-around time constraints for the aircraft.

When treatment is completed, the arms (5) are retracted to the stowed position. The apparatus of this disclosure is then transported back to the storage facility and plugged back into the external power source.

Some Alternative Embodiments

The following are representative examples of alternative embodiments and additional features, but are not intended to be all inclusive.

UVC sources may be fluorescent lamps, Light Emitting Diodes (LED), pulsed Xenon and other technologies known to produce ultraviolet light in the germicidal range.

The trolley has an estimated weight of approximately 75 pounds. A motor assist for pushing the trolley may be incorporated to ease in its mobility on and off the aircraft.

The UVC laden arms are foldable to substantially within the "footprint" of the trolley during transportation on and off the aircraft and for stowage. The arms extend laterally and perpendicular to the aisle at variable distance from the trolley. The two arms extend laterally independently to accommodate asymmetric seating configurations. There are a multitude of known mechanisms that allow this feature and some are illustrated within this application. More elaborate telescoping/folding/rolling or otherwise extensible mechanisms can be incorporated into the design and the disclosure includes such variations. The arms function independently of each other to optimally treat aircraft that may have different numbers of seats on each side of the aisle.

Because UVC light is potentially damaging to human skin and eyes, an onboard detection, warning and abort system is preferred. Sensors that monitor motion and heat or visual pattern recognition can be incorporated to detect human presence within a potentially dangerous radius of the device. Audible and visible alarms alert the human to the potential danger. The device stops and the UVC sources are depowered to prevent possible injury. Similarly, cameras can be included to remotely monitor the trolley's progress. UVC does not penetrate clothing, plastics or glass and very simple personal protective gear covering all skin and a simple visor would allow a worker to be safely adjacent to the trolley.

Programming may involve varying levels of automation. For example, one may program for the cabin of a 777 aircraft and the controller determines the direction, speed, number of rows, the desired extension of the arms and height of the UVC sources for the overhead bins. Less sophisticated programming may have variable row numbers, seats per row, speed of trolley travel, depending upon level of contamination etc.

A more sophisticated travel path may also be anticipated and programmed. For example, the arms may be programmed to follow the contours of the passenger seat, going up and down around the seat backs and even down to the floor to bring the UVC sources into closer proximity to contaminated sources.

In the method, the device and apparatus is positioned to expose the UV source in a positioned to expose the components of the aircraft desired to be sanitized. There can also be a cleaning component with the apparatus and a waste container or tank with the device. The exposure of the cleaning component and the interior of the waste container or tank, operates to control the proliferation of microorganisms and the generation of odor.

The extensible arms have the ability to disinfect surfaces that are not traveled over, but are remote from the traveled surface. Those surfaces, like seats, seat backs and tray tables cannot be traveled over and could not be sanitized are sanitized by the disclosed device which has those extensible arms.

An alternative embodiment could have the arms going up and down between seatbacks as the device travels in the aisle to get the arms closer to the sitting surface.

Surfaces like seats, seat backs and tray tables cannot be traveled over. Such surfaces could not be sanitized by a device that directs UV radiation to the surface on which it travels. The disclosed device, with extensible arms, allows such surfaces to be sanitized.

An alternative embodiment could have the arms going up and down between seatbacks as the device travels in the aisle to get the arms closer to the seat surfaces.

An alternative embodiment is a permanent installation onboard an aircraft with a storage compartment. There can be a configuration of the disclosure where the device would be stowed in a closed compartment and rather than wheels, for example a ceiling mounted rail system allows the device to travel fore and aft in the passenger compartment. An advantage to this system is that the aircraft can be sanitized regardless of whether the airport has functioning devices. A further advantage is apparent in case of an on-board inflight release of a pathogen, whether accidental/unintentional or bioterrorism. By activating an onboard device, with passengers shielded, an aircraft can be "sanitized" inflight prior to landing. This would avoid release of potential pathogens at the destination and neutralize the threat prior to human inoculation.

Many different formats are possible for the disclosure. It is therefore to be understood that within the scope of the appended claims the disclosure may be practiced otherwise than as specifically described.

What is claimed is:

1. A device for operating a movable UVC emitting cart without personal UVC exposure to an operator of the cart for sanitizing a surface while moving, the device comprising:

a mobile body configured to travel over a surface; and a source of UV radiation mounted to the mobile body and configured to direct UV radiation to the surface at a predetermined dosage while the cart is travelling;

an arm mounted to the mobile body, a UV lamp mounted on the arm, the arm being extendable from the mobile body to a position adjacent an area for sanitizing and the UV lamp being directed to the area for sanitizing, and a UVC protective operator shield connected to the mobile body, the operator shield being operable to encompass the operator and effectively isolate the operator from UVC exposure dosage while the cart is travelling;

the shield being an independent element directly attached and mounted with the mobile body in a removed position from the mounting of the arm to the mobile body, and the arm and the shield being movable independently of each other, and the shield being for extension away from the mobile body in a rearwards direction relative to the mobile body and in a direction away from the UV lamp, and the shield containing no UVC source.

2. The device as claimed in claim 1 wherein in one position of the shield there is a physical barrier to permit operator access to a control panel to permit UVC activation only when the shield is in a deployed position, and including at least one of interlock switches, and/or proximity sensor switches to permit UVC powering only when the shield is in the deployed position.

3. A device for operating a UVC emitting cart without personal UVC exposure to an operator of the cart for sanitizing a surface, the device comprising:
a mobile body configured to travel over a surface; and
a source of UV radiation mounted to the mobile body and configured to direct UV radiation to the surface at a predetermined dosage;
an arm mounted to the mobile body, a UV lamp mounted on the arm, the arm being extendable from the mobile body to a position adjacent an area for sanitizing and the UV lamp being directed to the area for sanitizing, and a UVC protective operator shield directly attached and connected to the mobile body, the operator shield being operable to encompass the operator and effectively isolate the operator from UVC exposure, and wherein the shield when stowed is narrowed to be about no greater than corresponding to a cart footprint, and when the shield is deployed, the width is to contain an operator's body width, and the shield being for extension away from the mobile body in a rearwards direction relative to the mobile body and away from the UV lamp, and the shield containing no UVC source.

4. The device as claimed in claim 1 including a safety feature including handles used to navigate the cart within the shield, and including momentary power switches embedded within the handles.

5. The device as claimed in claim 1 wherein the operator shield is collapsible to allow stowage into a smaller volume, and a mechanism operable to deploy the operator shield.

6. The device as claimed in claim 1 wherein the operator shield provides a physical barrier to access a control panel to permit UVC activation only when the shield is in a deployed position, and includes at least one of interlock switches, and/or proximity sensor switches to permit UVC powering only when the operator shield is deployed.

7. The device as claimed in claim 1 wherein the operator shield has a pair of spars that pivot at angled axes, and selectively when stowed, the distance between the spars is narrowed corresponding to the UVC emitting cart footprint, and when the operator shield is deployed, the distance between the spars is wide enough to contain an operator's body width.

8. The device as claimed in claim 1 including a safety feature including handles used to navigate the cart within the operator shield, including momentary UVC light power switches embedded within the handles.

9. A device for operating a UVC emitting cart without personal UVC exposure to an operator of the cart for sanitizing a surface, the device comprising:
a mobile body configured to travel over a surface; and
a source of UV radiation mounted to the mobile body and configured to direct UV radiation to the surface at a predetermined dosage;
an arm mounted to the mobile body, a UV lamp mounted on the arm, the arm being extendable from the mobile body to a position adjacent an area for sanitizing and the UV lamp being directed to the area for sanitizing, and a UVC protective operator shield directly attached and connected to the mobile body, the operator shield being operable to encompass the operator and effectively isolate the operator from UVC exposure, including a sensor for measuring the distance and/or power of the UVC lamps relative to the surface and controlling the amount of power and distance of the lamps from the surface and/or UVC energy transmitted to the surface; and wherein the shield is a multisided enclosure that separates the operator from the UVC exposure, and extendable from the mobile body in a rearwards direction relative to the mobile body, the shield containing no UVC source, and being non-releasably connected to the cart.

10. An ultraviolet disinfection cart comprising:
a mobile cart body having a footprint sized to permit an operator to navigate the cart along an aisle between a plurality of seats, the cart body carrying therein a power supply for UVC lamps supported by the cart and operation of the cart body;
one or more arms extendible from the cart body from a retracted position within and over the footprint of the cart body each to an extended position over one or more of the seats, at least one of the one or more arms carrying one or more of the UVC lamps; and configured to direct UV radiation to the surface at a predetermined dosage while the cart is travelling along an aisle, and
a UV protective operator shield operably directly attached and connected to the cart body separating and isolating the operator of the cart from UVC light produced by the UVC lamps dosage while the cart is travelling;
the shield being an independent element mounted with the mobile body in a removed position from the mounting of the arms to the mobile body, and the arms and the shield being movable independently of each other, and the shield being for extension away from the mobile body in a rearwards direction relative to the mobile body and in a direction away from the UVC lamp, and the shield containing no UVC source.

11. The disinfection cart according to claim 10 wherein the UV protective operator shield is a rigid multi sided structure configured to partially surround the operator during cart movement and prevent operator access to a control panel in the mobile body for operation of the UVC lamps unless the operator shield is in a deployed position.

12. The disinfection cart according to claim 10 wherein the UV protective operator shield is a foldable collapsible structure fastened to the mobile body, and extendable from the mobile body solely in a rearwards direction relative to the mobile body.

13. An ultraviolet disinfection cart comprising:
a mobile cart body having a footprint sized to permit an operator to navigate a path for disinfection of an environment around the footprint of the cart as the cart moves forwardly, a power supply source for UVC lamps supported by the cart and for operation of the cart body;
one or more arms extendible from the cart body from a retracted position within the footprint of the cart body to an extended position beyond the footprint of the cart body and over an area for disinfection, at least one of the one or more arms carrying one or more of the UVC lamps, and configured to direct UV radiation to the surface at a predetermined dosage while the cart is travelling along the path; and a UV protective operator shield operably directly attached and -connected to the cart and extendable rearwardly from the cart and wherein the operator shield operably separates and effectively prevents exposure to the operator located behind the UV protective operator shield to UVC light produced by the UVC lamps dosage while the cart is travelling; the shield being an independent element mounted with the mobile body in a removed position from the mounting of the arms to the mobile body, and the arms and the shield being movable independently of each other.

14. The disinfection cart according to claim 13 wherein the footprint is sized to permit an operator to navigate the cart along an aisle between a plurality of seats while the operator is shielded from UVC light produced by the UVC lamps by the protective shield, and wherein the area for disinfection includes one or more of the seats and the shield is extendable from the mobile body solely in a rearwards direction relative to the mobile body.

15. An ultraviolet disinfection cart comprising:

a mobile cart body having a footprint sized to permit an operator to navigate a path for disinfection of an environment around the footprint of the cart as the cart moves forwardly, a power supply source for UVC lamps supported by the cart and for operation of the cart body;

one or more arms extendible from the cart body from a retracted position within the footprint of the cart body to an extended position beyond the footprint of the cart body and over an area for disinfection, at least one of the one or more arms carrying one or more of the UVC lamps; and a UV protective operator shield operably directly attached and connected to the cart and extendable rearwardly of the cart and wherein the operator shield operably separates and effectively prevents exposure to the operator located behind the UV protective operator shield to UVC light produced by the UVC lamps, and wherein the operator shield includes a material and a support fastened to the mobile body for supporting the material so as to extend at least around a front and sides of the operator when deployed and the shield being for extension away from the mobile body in a rearwards direction relative to the mobile body and away from the UV lamp, and the shield containing no UVC source.

16. The device as claimed in claim 1 wherein the shield is a multisided enclosure that separates the operator from the UVC exposure, and being non-releasably connected to the cart.

17. The device as claimed in claim 3 wherein the shield is a multisided enclosure that separates the operator from the UVC exposure, and being non-releasably connected to the cart.

18. The device as claimed in claim 10 wherein the shield is a multisided enclosure that separates the operator from the UVC exposure, and being non-releasably connected to the cart.

19. The device as claimed in claim 13 wherein the shield is a multisided enclosure that separates the operator from the UVC exposure, and extendable from the mobile body in a rearwards direction relative to the mobile body, the shield containing no UVC source, and being non-releasably connected to the cart.

20. The device as claimed in claim 15 wherein the shield is a multisided enclosure that separates the operator from the UVC exposure, and being non-releasably connected to the cart.

21. The device as claimed in claim 1 wherein the cart includes a front face, opposite side faces, a back face, having a table extending between the front face, side faces and back face, and the arm extends transversely from a side face in a transverse direction relative to the cart thereby to direct UVC on a surface to the side of the cart, and the shield extends from the cart rearwardly from the back face above and below the table thereby to shield a person behind the cart from UVC exposure.

22. The device as claimed in claim 1 wherein the shield is essentially transparent to visual light over the greater area of the shield.

23. The device as claimed in claim 1 wherein the shield is collapsible.

24. The device as claimed in claim 1 wherein the shield includes hinging in an essentially horizontal line with the cart thereby to permit opening and closing of the shield.

25. The device as claimed in claim 1 wherein the cart includes wheels to facilitate forward travel on a trajectory on the surface, the trajectory being defined by the cart width and the shield extends rearwardly further than the cart width and is suspended rearwardly from the travelling cart and above the surface on which the cart travels and permits an operator to follow the cart trajectory and be contained within the shield during the forward travel of the cart.

26. A device for operating a movable UVC emitting cart without personal UVC exposure to an operator of the cart for sanitizing a surface while moving, the device comprising:

a mobile body configured to travel over a surface;

a source of UV radiation mounted to the mobile body and configured to direct UV radiation to the surface at a predetermined dosage while the cart is travelling; and an arm mounted to the mobile body, a UV lamp mounted on the arm, the arm being extendable from the mobile body to a position adjacent an area for sanitizing and the UV lamp being directed to the area for sanitizing, and a UVC protective operator shield connected to the mobile body, the operator shield being operable to encompass the operator and effectively isolate the operator from UVC exposure dosage while the cart is travelling;

the shield being an independent element directly attached and mounted with the mobile body in a removed position from the mounting of the arm to the mobile body, and the arm and the shield being movable independently of each other, and the shield being for extension away from the mobile body in a direction away from the UV lamp, and the shield containing no UVC source.

27. A device for operating a movable UVC emitting cart without personal UVC exposure to an operator of the cart for sanitizing a surface while moving, the device comprising:

a mobile body configured to travel over a surface;

a source of UV radiation mounted to the mobile body and configured to direct UV radiation to the surface at a predetermined dosage while the cart is travelling; and a UV lamp mounted on the mobile body to a direct UVC to a position transverse to the direction of travel of the cart and to an area for sanitizing and the UV lamp being directed to the area for sanitizing, and a UVC protective operator shield connected to the mobile body, the operator shield being operable to encompass the operator and effectively isolate the operator from UVC exposure dosage while the cart is travelling;

the shield being an independent element directly attached and mounted with the mobile body in a removed position from the UV lamp on the mobile body, and the shield being for extension away from the mobile body in a direction away from the UV lamp, and the shield containing no UVC source.

* * * * *